(12) United States Patent
Hamdi et al.

(10) Patent No.: US 7,468,355 B2
(45) Date of Patent: *Dec. 23, 2008

(54) METHODS FOR INHIBITING CANCER AND SCAR FORMATION

(75) Inventors: Hamdi K. Hamdi, Los Angeles, CA (US); Raquel Castellon, Norwalk, CA (US)

(73) Assignee: H2RC Corporation, Los Angeles, CA (US)

( * ) Notice: Subject to any disclaimer, the term of this patent is extended or adjusted under 35 U.S.C. 154(b) by 625 days.

This patent is subject to a terminal disclaimer.

(21) Appl. No.: 10/712,423

(22) Filed: Nov. 13, 2003

(65) Prior Publication Data

US 2004/0097428 A1   May 20, 2004

Related U.S. Application Data

(63) Continuation-in-part of application No. 10/657,414, filed on Sep. 8, 2003, now abandoned, which is a continuation of application No. 10/153,003, filed on May 22, 2002, now Pat. No. 6,632,798.

(60) Provisional application No. 60/431,780, filed on Dec. 9, 2002.

(51) Int. Cl.
*A61K 31/70* (2006.01)
*A61K 31/35* (2006.01)

(52) U.S. Cl. .................................. 514/27; 514/460

(58) Field of Classification Search .................. 514/27, 514/460
See application file for complete search history.

(56) References Cited

U.S. PATENT DOCUMENTS 6,117,844 A     9/2000  Fredrickson
6,358,542 B2 *  3/2002  Cuomo et al. ............... 424/777
6,361,803 B1    3/2002  Cuomo et al.
6,437,004 B1    8/2002  Perricone
6,440,465 B1    8/2002  Meisner
2002/0004077 A1 1/2002  Cuomo et al.
2003/0108651 A1* 6/2003 Crea .......................... 426/615

OTHER PUBLICATIONS

Gura (Science, 1997, 278:1041-1042).*
Johnson et al (British J. of Cancer 2001, 84(10) 1424-1431).*
Pancreatic Cancer Update Jan. 19, 2006.*
McCarty, Med. Hypothesis, vol. 50(6), pp. 511-514 (abstract). Jun. 1998.
Visioli et al., Biochem. Biophys. Res. Commun., vol. 247(1), pp. 60-64 (abstract), Jun. 9, 1998.
de la Puerta et al., Biochem. Pharmacol., vol. 57(4), pp. 445-449 (abstract), Feb. 15, 1999.
Park et al., Chem Pharm Bull (Tokyo), vol. 47(7), pp. 1029-1031 (abstract), Jul. 1999.
Owen, R.W., Olives and olive oil in cancer prevention; European Journal of Cancer Prevention; 2004; pp. 319-326; vol. 13, No. 4.
Owen, R. W., Olive-oil consumption and health: the possible role of antioxidants; The Lancet Oncology; Oct. 2000; pp. 107-112; vol. 1.
Park, Hee-Juhn; Studies on constituents with cytotoxic activity from stem bark of Syringa velutina; Chem. Pharm. Bull.; Jul. 1999; pp. 1029-1031; vol. 47, No. 7.

* cited by examiner

*Primary Examiner*—Michael G. Hartley
*Assistant Examiner*—Shirley V Gembeh
(74) *Attorney, Agent, or Firm*—Stetina Brunda Garred & Brucker

(57) ABSTRACT

Methods for inhibiting cancer, scar formation, disrupting the cellular cytoskeleton, and conferring resistance from infection are disclosed. Such methods comprise the administration of oleuropein and/or the products of its hydrolysis in therapeutically effective amounts. To that end, a variety of pharmaceutical formulations and routes or administration are disclosed and may be utilized to treat a wide variety of diseases.

20 Claims, 8 Drawing Sheets

Figure 2
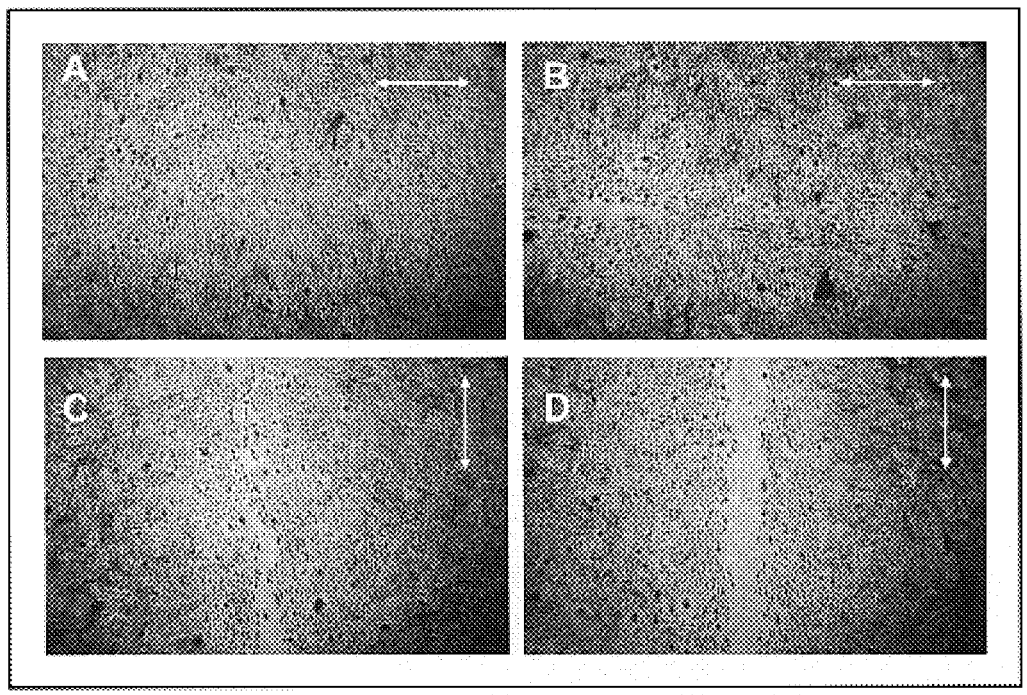
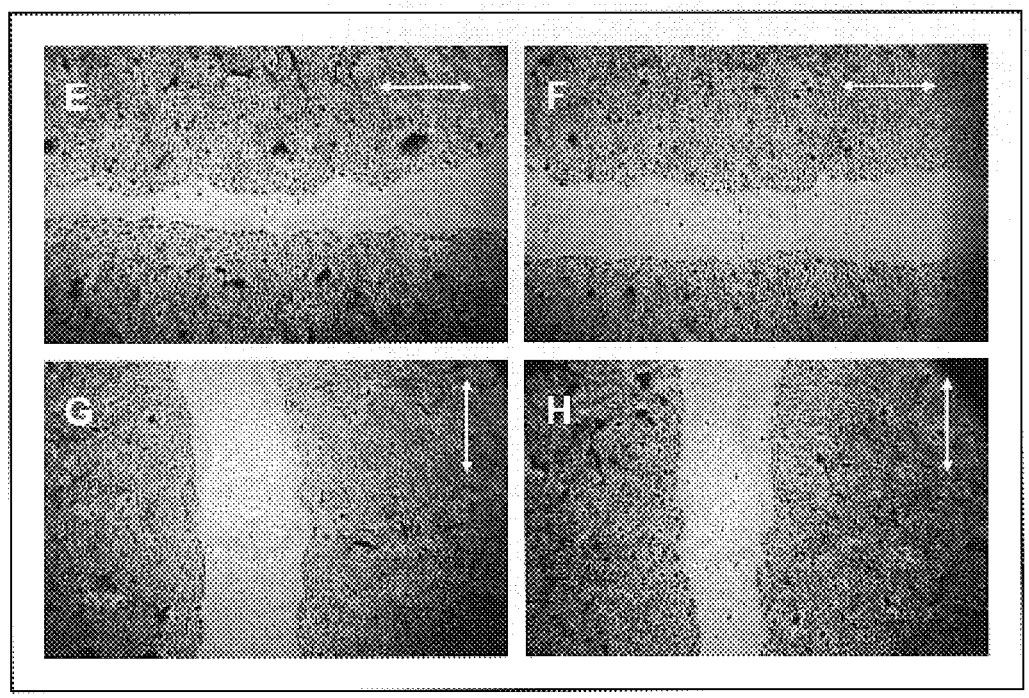

METHODS FOR INHIBITING CANCER AND SCAR FORMATION

CROSS-REFERENCE TO RELATED APPLICATIONS

The present application is a continuation-in-part application claiming priority to U.S. patent application Ser. No. 10/657,414 entitled Methods for Inhibiting Angiogenesis, filed on Sep. 8, 2003 now abandoned, which is a continuation of U.S. patent application No. 10/153,003 entitled Methods for Inhibiting Angiogenesis, filed May 22, 2002, now issued as U.S. Pat. No. 6,632,798 and also claims priority to United States Provisional Patent Application Serial No. 60/431,780, entitled Methods for Inhibiting Cancer, Filed Dec. 9, 2002.

BACKGROUND OF THE INVENTION

The present invention is directed to methods for efficiently inhibiting cancer, scar formation, disrupting the cellular cytoskeleton, and conferring resistance from infection. More particularly, this invention relates to methods of treating diseases associated with cancer, scar formation and infections and to delivering this activity in live animals including humans having such diseases.

Cancer is the unregulated growth of cells and tumors. Although cell survival, division, mobility and invasiveness are natural and regulated processes in wound healing, fetal and embryonal development and in the formation of the corpus luteum, endometrium and placenta. These processes are vital to health and growth and are very well regulated by oncogenes, tumor suppressor genes and a myriad of growth factors, while they can, however, when unregulated lead to tumor formation. Genetic alterations, however, caused by both heritable and environmental factors can lead to pathogenic and unregulated growths and tumors. Pathogenic cellular dysregulation leading to cancer and other diseases is unwanted and is the target for therapeutic interventions.

BRIEF SUMMARY OF THE INVENTION

In one feature, this invention relates to a method of inhibiting cancer cells, the method comprising contacting a cell, tissue or organ which has cancer cells with a therapeutic and effective amount of a compound of Formula I. Compounds of Formula I have the following general formula:

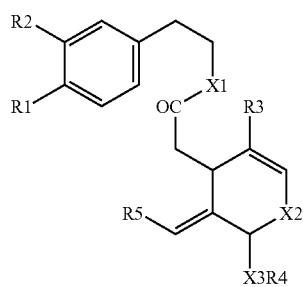

Formula I

In formula I, R1 and R2 are functional groups including, but not limited to, hydroxyl, —NH2, and —SH groups.

In formula I, R3 is a functional group including, but not limited to, hydrogen, C1-C6-alkyl, C2-C6-alkenyl, C2-C6-alkynyl, aryl, hydroxyl, C1-C6-alkoxy, halogen, NO2, NH3, and COOCH3.

In formula I, R4 is a functional group including, but not limited to, hydrogen, C1-C6-alkoxy, glucose, B-D-glucopyranose, C1-C6-alkyl, C2-C6-alkenyl, C2-C6-alkynyl, aryl, hydroxyl, halogen, NO2, NH3, carbohydrate, amino acid, nucleotide and lipid.

In formula I, R5 is a functional group including, but not limited to, hydrogen, C1-C6-alkyl, C2-C6-alkenyl, C2-C6-alkynyl, aryl, hydroxyl, C1-C6-alkoxy, halogen, NO2, NH3, and CH3.

In formula I, X1-X3, are functional groups including, but not limited to, oxygen, sulfur, —CH2-, or carboxy, which can be different but preferably are identical functional groups.

In a preferred embodiment of the invention, the compound of formula I is oleuropein with formula C25H32O13, as described in the tenth edition of THE MERK INDEX with monograph number 6709, and shown in Formula II.

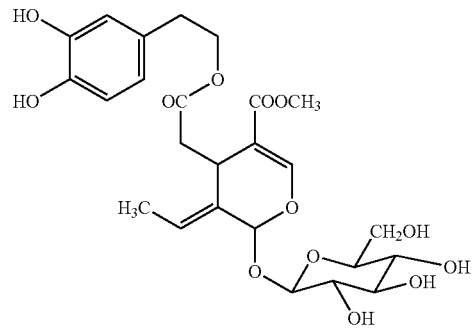

Formula II

A plant extract can be derived which can comprise any of the ethanolic, acetone, inorganic and organic acid or base and/or aqueous extraction of plant extract and will contain oleuropein, the compound shown in formula II. Plant extract is derived from plants including but not limited to the leaves, buds, fruit, wood, bark and roots of the olive tree *Olea europaea* L., the privet tree, *Ligustrum obtusifolium* (Oleaceae), etc.

In another aspect, this invention relates to a method for potently inhibiting cancer cells in a tissue or organ, the method comprising contacting the cell with a pharmaceutical composition containing oleuropein, the compound shown in formula II or a derivative thereof as shown in formula I or products of its hydrolysis, which can include but are not limited to oleuropein aglycone, elenolic acid, beta-3,4-dihydroxyphenyethyl alcohol and methyl-o-methyl elenolate or a pharmaceutical composition thereof, in an amount sufficient to inhibit cancer. In a presently preferred embodiment, the cell is in a live organism. Such composition may comprise an ethanolic, acetone, inorganic and organic acid or base and/or aqueous solution of plant extract or a derivative of the ethanolic, acetone, inorganic and organic acid or base and/or aqueous solution or a component thereof, In yet another aspect, this invention relates to a method of treating cancer diseases mediated by or associated with undesired and uncontrolled growth, survival, replication, motility, invasion, and metastasis of cancer cells, the method comprising administering to a live animal an effective dose of a pharmaceutical composition containing oleuropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, solution in a dosage sufficient to inhibit cancer cell survival, replication, growth, motility, invasion, and metastasis. These methods are useful for ameliorating the effects of conditions that are characterized by abnormal or undesirable cancer cell proliferation and/or migration. Such composition may comprise an ethanolic, acetone, inorganic and organic acid or base and/or aqueous solution of plant extract X or a derivative of the ethanolic, acetone, inorganic and organic acid or base and/or aqueous or a component thereof.

In yet another aspect, this invention relates to a method for the selective targeting of cancer cells by the glucose moiety of oleuropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, in an amount sufficient to inhibit cancer. According to such method, oleuropein enters the cell by facilitated diffusion through the glucose transporter (GLUT). There are currently 12 GLUT proteins with various glucose affinities and tissue specific distributions. It has been reported that human malignancies are characterized by elevated glucose uptake and utilization, which was based on enhanced expression of multiple GLUT isoforms. For example GLUT1 and/or GLUT3 mRNA was found to be increased in cancers of the breast, esophagus and colon. Cancer cells overexpress GLUT proteins and are thus more likely to uptake oleuropein, which contains a glucose molecule.

In yet another aspect, this invention relates to a method for disrupting and preventing the reorganization of the cytoskeleton whereby an animal cell rounds up and is unable to divide, move, or invade, the method comprising contacting the cell with a pharmaceutical composition containing oleuropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, in an amount sufficient to inhibit cancer. In a presently preferred embodiment, the cell is in a live organism. Such composition may comprise an ethanolic, acetone, inorganic and organic acid or base and/or aqueous solution of plant extract or a derivative of the ethanolic, acetone, inorganic and organic acid or base and/or aqueous solution or a component thereof.

In yet another aspect, this invention relates to a method for disrupting a cell's cytoskeleton whereby an animal cell is resistant to infection by bacteria, virus or parasitic organisms, the method comprising contacting the cell with a pharmaceutical composition containing oleuropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, in an amount sufficient to make the cell resistant to infection. Such composition may comprise an ethanolic, acetone, inorganic and organic acid or base and/or aqueous solution of plant extract x. or a derivative of the ethanolic, acetone, inorganic and organic acid or base and/or aqueous solution or a component thereof. According to such method, it is believed the animal cell cytoskeleton including the cytoskeleton of human cells is targeted during infection by a variety of viral, bacterial and parasitic pathogens. For example the pathogen listeria monocytogenes, a bacterium that is internalized by host cells, induces the polymerization of actin (a cytoskeletal protein) at its surface, and uses the energy derived from polymerization to power intracellular motility and cell to cell spread. oleuropein's inhibition of the animal cell's cytoskeletal reorganization can prevent the spread of infectious disease. In a presently preferred embodiment, the cell is in a live organism.

Other features, objects and advantages of the invention and its preferred embodiments will become apparent from the detailed description which follows.

BRIEF DESCRIPTION OF THE DRAWINGS

These as well as other features of the present invention will become more apparent upon reference to the drawings wherein:

FIG. 2. Cell migration assay. In this assay, renal adenocarcinoma cells are cultured to confluency and then wounded with a sterile wooden stick to form what appears as a road. The cells are then allowed to incubate and migrate across this road to repair the wound in the culture. Untreated cells shown in (A), (B), (C), (D) have succesfully closed the wound area. In comparison cells treated with 0.01% oleuropein shown in (E), (F), (G), and (H) did not effectively close the wound. The arrows indicate the orientation of the wound.

DETAILED DESCRIPTION OF THE INVENTION

Figure 1:
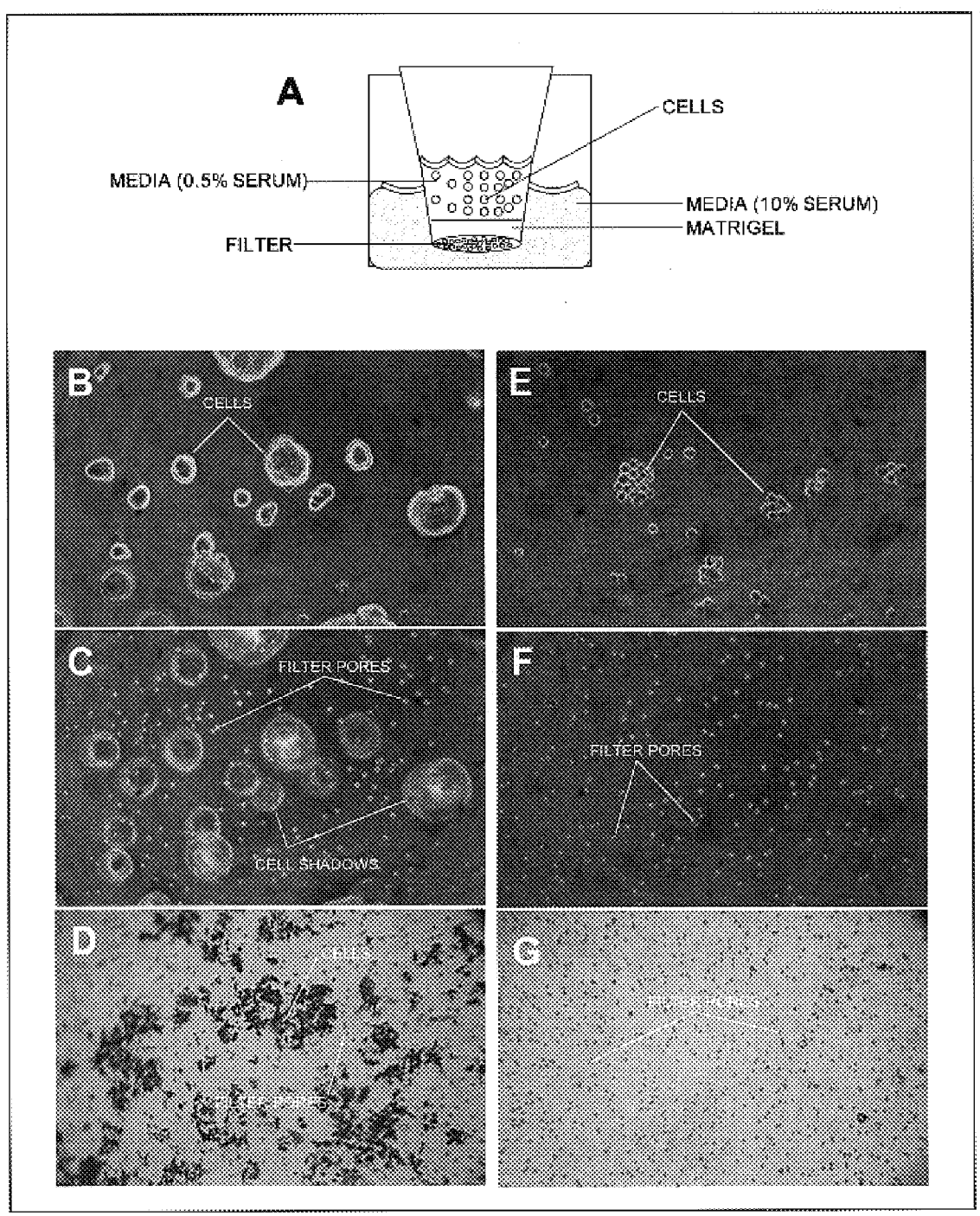
FIG. 1. Matrigel Invasion assay. Studying the most invasive cancer (colon) on matrigel we show the effect of oleuropein. Cells treated with 0.1% oleuropein were completely stopped from invading the gel and adhering to the filter on the bottom side. A schematic of the matrigel invasion chamber is shown in (A). The cell layer and the filter plane were photographed during the course of the experiment. The invasion chamber containing untreated cells is shown in (B) and (C) photographed at the cell and filter planes respectively. As evident in the photograph, cell shadows can be seen in the focal plane of the filter indicating their proximity to the filter and their mobility through the matrigel layer. In contrast photographs of the filter plane (F) in the invasion chamber containing cells treated with oleuropein do not contain cell shadows. In fact the cells were photographed at a much higher plane in the matrigel and did not appear to be mobile in matrigel (E). At the endpoint of the experiment the matrigel was completely removed. The filter was fixed, stained and photographed. Cells that have migrated across the matrigel layer and adhered to the underside of the filter are shown in (D) and (G). The filters obtained from the chambers which contained oleuropein (G) were devoid of cells, indicating that none of the cells reached the filter. The filters from the non-treated chambers contained cells that penetrated the matirgel and adhered to the filter (D).

The detailed description set forth below is intended as a description of the presently preferred embodiment of the invention, and is not intended to represent the only form in which the present invention may be practiced or utilized. The description sets forth the functions and sequences of steps for practicing the invention. It is to be understood, however, that the same or equivalent functions and sequences may be accomplished by different embodiments and that the equivalent functions and sequences are also intended to be encompassed within the scope of the invention.

A. Definitions

The term "animal" refers to an organism with a closed circulatory system of blood vessels and includes birds, mammals, amphibians, fish and reptiles. The term "animal" used here also includes human subjects.

The term "resistance to infection" refers to a property, which oleuropein confers on animal cells, which makes those cells resist infectious agents like bacteria, viruses, and parasites. The conference of this property by oleuropein is independent of its direct action on microbes themselves, which has been well documented in the literature.

The term "cancer" refers to the uncontrolled and uregulated growth of cells in the context of tissues, organs or the human body.

The term "metastasis" refers to the process by which tumor cells are spread to distant parts of the body. The term is also used herein to refer to a tumor that develops through the metastatic process.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

"An amount sufficient," "an effective amount," "therapeutically effective amount" or "anti-angeogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the animal having the cancer wherein the improvement can be ascribed to treatment with the compounds of the present invention. The improvement can be either subjective or objective. For example, if the animal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

The term "alkyl" is used herein to refer to a branched or unbranched, saturated or unsaturated, monovalent hydrocarbon radical having from 1-12 carbons and preferably, from 1-6 carbons. When the alkyl group has from 1-6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., CF3), hydroxy, amino, alkoxy, alkylamine, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "S-alkyl" is used herein to refer to the group —SR, where R is lower alkyl or substituted lower alkyl as defined herein.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

"Substituted aryl" refers to aryl as just described including one or more functional groups such as lower alkyl, acyl, halogen, alkylhalos (e.g. CF3), hydroxy, amino, alkoxy, alkylamine, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "halogen" is used herein to refer to fluorine, bromine, chlorine and iodine atoms.

The term "hydroxy" is used herein to refer to the group —OH.

The term "amino" is used to refer to the group —NRR', where R and R' may independently be hydrogen, alkyl, substituted alkyl, aryl, substituted aryl or acyl.

The term "nitro" is used herein to refer to the group —NO2.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkenyl" is used herein to refer to an unsaturated branched, straight chain or cyclic monovalent hydrocarbon radical having at least one carbon-carbon double bonds. The radical can be in either the cis or trans conformation about the double bond(s). Suitable alkenyl radicals include, for example, ethenyl, propenyl, isopropenyl, cyclopropenyl, butenyl, isobutenyl, cyclobutenyl, tert-butenyl, pentenyl, hexenyl, etc.

The term "alkynyl" is used herein to refer to an unsaturated branched, straight chain or cyclic monovalent hydrocarbon radical having at least one carbon-carbon triple bond. Suitable alkynyl radicals include, for example, ethynyl, propynyl, butynyl, isobutynyl, pentynyl, hexynyl, etc.

The term enantiomer is used herein to refer to one of a pair of molecular entities which are mirror images of each other and non-superposable.

B. Compounds

The present invention relates to the discovery that compounds of formula I inhibit the growth of cancer cells and are useful for treating cancer diseases. Compounds of Formula I have the following general formula:

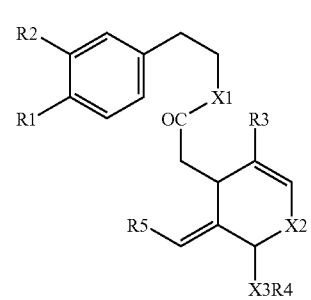

Formula I

Wherein R1, R2, R3, R4, R5, and X1, X2, and X3 are as defined above. In a preferred embodiment of the invention, the compound of formula I is oleuropein as shown below in Formula II:

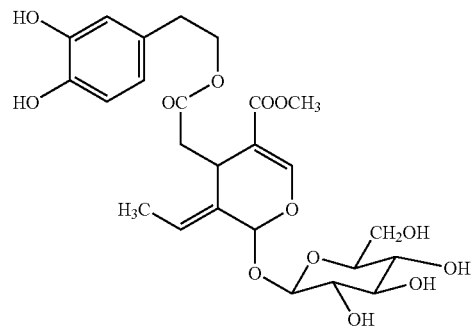

Oleuropein, the compound used in the present invention can be readily obtained from plants including but not limited to the olive tree *Olea europaea* L. and the privet tree, *Ligustrum obtusifolium* (Oleaceae).

Compounds suitable for use in the methods of the present invention can readily be identified using in vitro and in vivo screening assays. Such assays may screen for the ability of a particular compound to inhibit the growth, motility and invasiveness of cancer cells or tumor production in vitro and in vivo. Alternatively such assays may screen for the ability of a particular compound to inhibit the cellular cytoskeleton leading to cell rounding. For instance, the matrigel invasion assay, which is described in more detail below, can be used to screen a given compound for its ability to inhibit cellular invasion of the extracellular matrix. This type of cellular invasion is a requisite for cancer establishment and growth. In the matrigel invasion assay as performed in this invention, cancer cells are seeded on matrigel, which is extracellular matrix. The cells are allowed to digest and invade the gel. Cells that have successfully invaded the matrigel stick to the underside of a filter, which contains pores. Monitoring the cell's invasion of the matrigel can be done using a microscope and focusing on the various planes of the chamber containing the cells. At the endpoint of the assay the matrigel is completely removed and the filter is fixed and stained to reveal the cells that have successfully penetrated the matrigel layer. Based on the number of number of cells on the filter one can assess the result of a compound's inhibitory effect on cellular invasiveness. This assay can be used to assess the anti-cancer properties of the compounds in this invention.

In another assay some types cells when grown on a high concentration of basement membrane matrix (matrigel®>10 mg/ml) undergo a series of morphological changes over a period of 48 hours. This allows the investigator to dissect the affects of compounds added to the culture through their action on these changes. During this process the cells change their morphology from flat, two-dimensional cells to three-dimensional tube-like networks. The tubes that are formed, however, are not stable and eventually collapse by retraction within 48 hours. Compounds added to the preformed tubes causing their disruption by rounding up the cells are understood to act on the cellular cytoskeleton. This assay can be used to assess the compound's disruptive effect on the cellular cytoskeleton in this invention. It will be readily apparent to those skilled in the art that the compounds in this invention can be administered alone, in the form of a pharmaceutically acceptable salt and/or in the form of a pharmaceutical composition.

C. Uses for the Compounds of the Present Invention

As explained above, the present invention relates to the discovery that the compounds of formula I or its preferred embodiment oleuropein, or its hydrolysis products are useful for inhibiting cancer cell survival, growth, motility and invasiveness and, in turn, for treating diseases associated with uncontrolled and unregulated cancer growths. As such, in one embodiment, the present invention provides a method of inhibiting uncontrolled and unregulated cancer cells, the method comprising contacting the cells with an effective amount, i.e., an anti-cancer amount, of a compound of formula I or it preferred embodiment oleuropein or its hydrolysis products or its hydrolysis products. In another embodiment, the present invention provides a method of inhibiting the cancer cells, the method comprising contacting a cell, tissue or organ containing the cancer cells with an effective amount of a compound of formula I or its preferred embodiment oleuropein or its hydrolysis products. In a presently preferred embodiment, the cells are in an animal subject.

This invention relates to a method of treating diseases associated with undesired and uncontrolled cancer, the method comprising administering to an animal an anti-cancer compound of formula I or its preferred embodiment oleuropein or its hydrolysis products in an amount, i.e., a dosage, sufficient to inhibit cancer. The particular dosage of a compound of formula I or its preferred embodiment oleuropein or its hydrolysis products required to inhibit cancer and/or cancer diseases will depend upon the severity of the condition, the route of administration, and related factors that will be decided by the attending physician. Generally, accepted and effective daily doses will be the amount sufficient to effectively inhibit cancer and/or cancer diseases. In this regard, the methods of the present invention will closely mimic those disclosed in Applicants' co-pending U.S. patent application Ser. No. 10/153,003 entitled Methods for Inhibiting Angiogenesis, filed May 22, 2002 and now in the issuance process. In this regard, Applicants expressly incorporate the teachings of U.S. patent application Ser. No. 10/153,003 herein by reference.

The methods of treatment provided by this invention are practiced by administering to an animal in need thereof a dose of a compound of formula I or its preferred embodiment or its hydrolysis products (or a pharmaceutically acceptable salt or solvate thereof) that is effective to inhibit cancer and/or cancer diseases. The term "inhibit" is used herein to include its generally accepted meaning which includes prophylactically treating a human subject from acquiring cancer and/or cancer diseases, and holding in check and/or treating existing cancer and/or cancer diseases. As such, the present invention includes both medical therapeutic and/or prophylactic treatment, as appropriate.

The methods of the present invention can be used to treat a wide variety of cancer diseases. Diseases known as cancer that can be treated using the methods of the present invention include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma and Thymic Carcinoma; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma, Childhood; Vulvar Cancer; Waldenstrom's Macroglobulinemia; Wilms' Tumor.

Methods in the present invention can also be used to confer resistance to infection on animal cells. By disrupting the animal cell's cytoskeleton, oleuropein, renders the cells resistant to infection by viral, bacterial, and parasitic organisms.

Diseases associated with blisters, ulcerations, scabs and scar formation can also be treated using the methods of the present invention. Diseases, which lead to ulcer formation and scar formation, include, but are not limited to, chemical, heat, and radioactive burns, scrapes and cuts, trauma, fibroids, cysts, keloid, acne, gastritis, vaginal, cervical, uterine, ovary, gastric, corneal, retinal, diabetic, AIDS-related scarring, iliac, and colon ulcers, interstitial lung disease, human fibrotic lung disease, human kidney disease, glomerular nephritis, nephritis associated with systemic lupus, peritoneal fibrosis, cystic fibrosis, liver fibrosis, myocardial fibrosis, pulmonary fibrosis, Grave's ophthalmopathy, drug induced ergotism, cardiovascular disease, cancer, Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, gynecological cancer, Kaposi's sarcoma, Hansen's disease, or inflammatory bowel disease not including collagenous colitis, renal fibrosis, abdominal adhesions, radiation induced fibrosis, obliterative bronchiolitis, silicosis lesions, or Tenon's capsule fibroproliferation, laser treatment for vascular birthmarks, tattoos, and traumatic scarring.

In a particularly preferred embodiment, the present invention relates to methods of administering compounds of formula I or its preferred embodiment oleuropein in combination with active immunotherapy (e.g., tumor vaccination).

Moreover, in accordance with the above methods, animal subjects to be treated therewith include, but are not limited to, humans, laboratory animals, domestic pets and farm animals.

D. Pharmaceutical Formulations/Routes of Administration

In the methods of the present invention, the compounds of formula I or its preferred embodiment oleuropein or its hydrolysis products can be delivered or administered to an animal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to depress, suppress or inhibit cancer or result in amelioration of symptoms associated with cancer diseases.

The compounds of formula I or its preferred embodiment oleuropein or its hydrolysis products, which are used in the methods of the present invention, can be incorporated into a variety of formulations for therapeutic administration. More particularly, compounds of formula I or its preferred embodiment oleuropein or its hydrolysis products can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

In addition, the compounds of formula I or its preferred embodiment oleuropein or its hydrolysis products can be formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

Compounds of formula I or its preferred embodiment oleuropein or its hydrolysis products can be administered alone, in combination with each other, or they can be used in combination with other known compounds (e.g., other anti-cancer drugs or other drugs, such as AZT, anti-inflammatories, antibiotics, corticosteroids, vitamins, etc.). For instance, the compound of formula I or its preferred embodiment oleuropein or its hydrolysis products can be used in conjunctive therapy with other known anti-angiogenic chemotherapeutic or antineoplastic agents (e.g., vinca alkaloids, antibiotics, antimetabolites, platinum coordination complexes, etc.). For instance, the compounds of formula I or its preferred embodiment oleuropein or its hydrolysis products can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known anti-angiogenic chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be infused are used in the formulation. Such penetrants are generally known in the art.

For oral administration, the compounds of formula I or its preferred embodiment oleuropein or its hydrolysis products can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Alternatively, other delivery systems for hydrophobic pharmaceutical compounds may be employed. Liposomes and emulsions are well known examples of delivery vehicles or carriers for hydrophobic drugs.

In addition, targeting of a marker on abnormal tumor vasculature can be employed. The targeting moiety when coupled to a toxic drug or radioisotope will act to concentrate the drug where it is needed. Ligands for tumor-associated vessel markers can also be used. For example, a cell adhesion molecule that binds to a tumor vascular element surface marker can be employed. Liposomes and other drug delivery systems can also be used, especially if their surface contains a ligand to direct the carrier preferentially to the tumor vasculature. Liposomes offer the added advantage of shielding the drug from most normal tissues, thereby reducing the inherent toxicity of many compounds. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity, and increased efficacy over non-targeted drug. Other targeting strategies include, but are not limited to, ADEPT (antibody-directed enzyme pro-drug therapy), GDEPT (gene-directed EPT) and VDEPT (virus-directed EPT). In ADEPT, the targeting of an inactive prodrug to a tumor mass is effected by an antibody against a tumor-associated marker. The enzyme milieu in or about the tumor transforms the prodrug into an active toxic agent that then acts on the tumor tissue. Similarly, differential gene expression or viral targeting at the tumor site is used to activate a prodrug into its active, toxic form in GDEPT and VDEPT, respectively. Other strategies include targeting differentially expressed genes, enzymes or surface markers that appear on tumor-associated vasculature, to effect control of tumor growth. Using the foregoing methods, the compounds of formula I or its preferred embodiment oleuropein or its hydrolysis products can be targeted to the tumor vasculature to effect control of tumor progression or to other sites of interest (e.g., endothelial cells).

Certain organic solvents such as dimethylsulfoxide also may be employed. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

Presently, it is contemplated that therapeutically effective amounts of the compounds utilized in the practice of the present invention can comprise anywhere between approximately 0.030 g to 20.000 g of such compound per kilogram mass of body weight of the subject.

EXAMPLES

The invention will be described in greater detail by way of specific examples. The following example is offered for illustrative purposes, and is not intended to limit the invention in any manner. Those of skill in the art will readily recognize a variety of noncritical parameters which can be changed or modified to yield essentially the same results.

Example 1

This example illustrates the anti-cancer properties of oleuropein in the matrigel invasion assay. The endpoint of the matrigel invasion assay is to the determination of the number of cells that invaded and digested the matrigel to reach the filter on the other end of the chamber. Such a quantitation would illustrate the invasiveness of the cancer cells by their ability to digest and invade the extracellular matrix. The decrease in the number of cells found on the filter as a result of the application of oleuropein indicates its anti-cancer properties.

Utilizing a Boyden chamber shown in the schematic (FIG. 1A), we deposited a top layer of matrigel at 10 mg/ml. Using the most invasive cancer (colon) cell line we seeded the cells on the matrigel top layer with or without oleuropein. The cells were allowed to migrate through the gel for 3 days during which the cell layer and the filter plane were photographed. At the endpoint of the experiment the matrigel layer was removed and the attached cells on the underside of the filter where fixed, stained and photographed. Cells treated with 0.1% oleuropein were completely stopped from invading the gel and adhering to the filter on the bottom side. The invasion chamber containing untreated cells is shown in (FIG. 1B) and (FIG. 1C) photographed at the cell and filter planes respectively. As evident in the photograph, cell shadows can be seen in the focal plane of the filter indicating their proximity to the filter and their mobility through the matrigel layer. In contrast photographs of the filter plane (FIG. 1F) in the invasion chamber containing cells treated with oleuropein do not contain cell shadows. In fact the cells were photographed at a much higher plane in the matrigel and did not appear to be mobile (FIG. 1E). Cells that have migrated across the matrigel layer and adhered to the underside of the filter are shown in (FIG. 1D) and (FIG. 1G). The filters obtained from the chambers, which contained oleuropein (FIG. 1G) were devoid of cells, indicating that none of the cells reached the filter. The filters from the non-treated chambers contained cells that penetrated the matirgel and adhered to the filter (FIG. 1D). Such result is indicative that oleuropein is an effective inhibitor of cancer cell invasion and is thus considered an anti-cancer compound.

Example 2

This example illustrates the anti-cancer properties of oleuropein in the cell migration assay. The endpoint of the cell migration assay is the determination of the number of cells that have migrated to close a wound produced in the culture dish. Such a quantitation would illustrate the mobility of cancer cells by their ability to completely close such a wound. The decrease in the number of cells found in the wound area as a result of the application of oleuropein indicates its anti-cancer properties.

In the classic wound assay, cells are cultured to confluency and then wounded with a sterile wooden stick to form what appears as a road. The cells are then allowed to incubate and migrate across this road to repair the wound in the culture. In this experiment we used renal adenocarcinoma cells. Untreated cells shown in FIGS. (2A), (2B), (2C), (2D) have successfully closed the wound area. In comparison cells treated with 0.01% oleuropein shown in FIGS. (2E), (2F), (2G), and (2H) did not effectively close the wound. Again showing oleuropein inhibiting cancer cell mobility and having anti-cancer properties.

Figure 3:
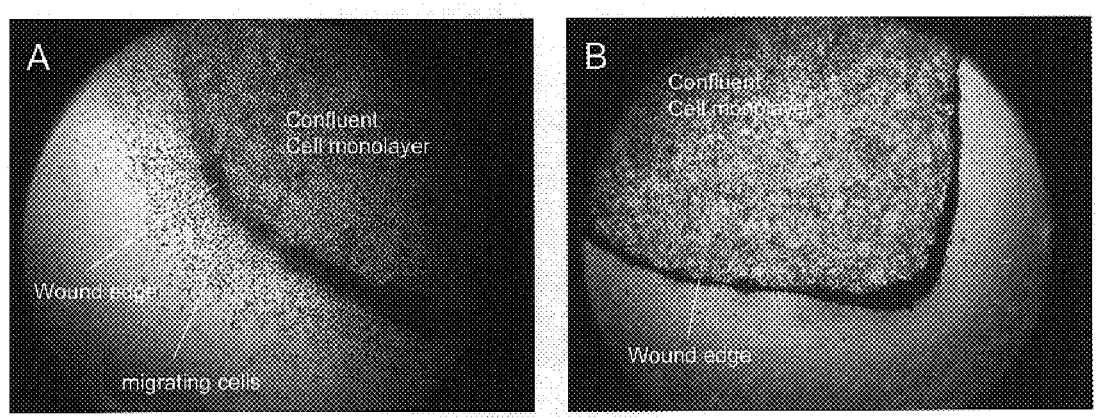
FIG. 3. A variation of the above cell migration assay of FIG. 2 is depicted. The wound in this assay was more extensive and formed a corner or curved edge. In this experiment malignant melanoma cells were grown to confluency and then wounded using a wooden stick in the fashion described above. Shown in (A) are untreated cells migrating in all directions over the plate. The migration of cells that were treated with a 0.01% solution of oleuropein (B) was completely halted. The wound edge in this wound assay can clearly be seen and is used to assess the advance of migrating cells.

A variation on the above cell migration assay, the wound assay was conducted with a more extensive wounded area and formed a corner or curved edge (FIG. 3). In this experiment malignant melanoma cells were grown to confluency and then wounded using a wooden stick in the fashion described above. Shown in (FIG. 3A) are untreated cells migrating in all directions over the plate. The migration of cells that were treated with a 0.01% solution of oleuropein (FIG. 3B) was completely halted. The wound edge in this wound assay can clearly be seen and is used to assess the advance of migrating cells. This again indicates the anti-cancer properties of oleuropein.

Figure 4:
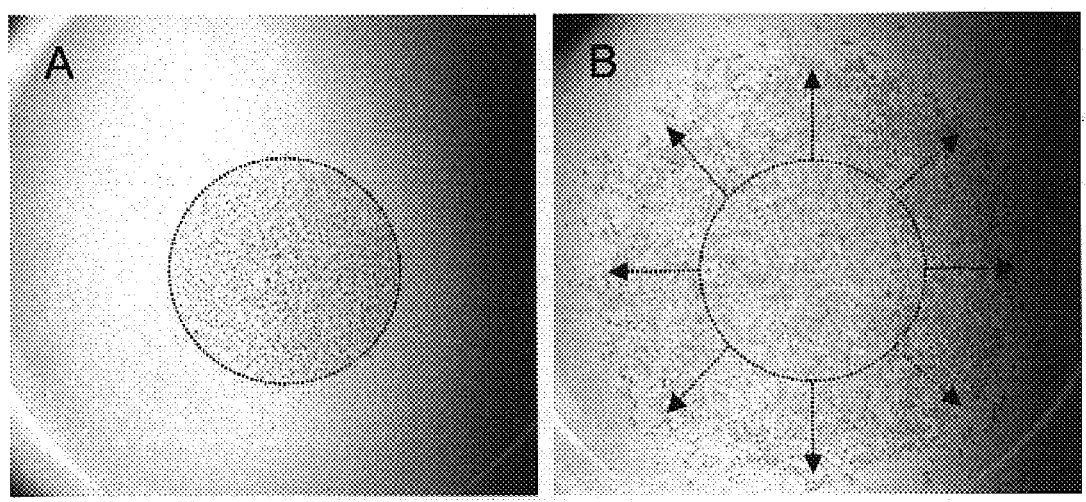
FIG. 4. A variation on the above experiment is depicted using the same cells as in FIG. 3 except plated as a circle. (A) Treated cells (0.01% oleuropein) did not migrate outside of the designated circle. (B) Untreated cells, however, migrated radially outwards and covered the plate.

In yet another variation on the above experiments melanoma cells were plated as a circle (FIG. 4). Treated cells (0.01% oleuropein) did not migrate outside of the designated circle. (FIG. 4A). Untreated cells, however, migrated radially outwards and covered the plate (FIG. 4B). Such outcome strongly suggests the anti-cancer properties of oleuropein.

Example 3

Figure 5:
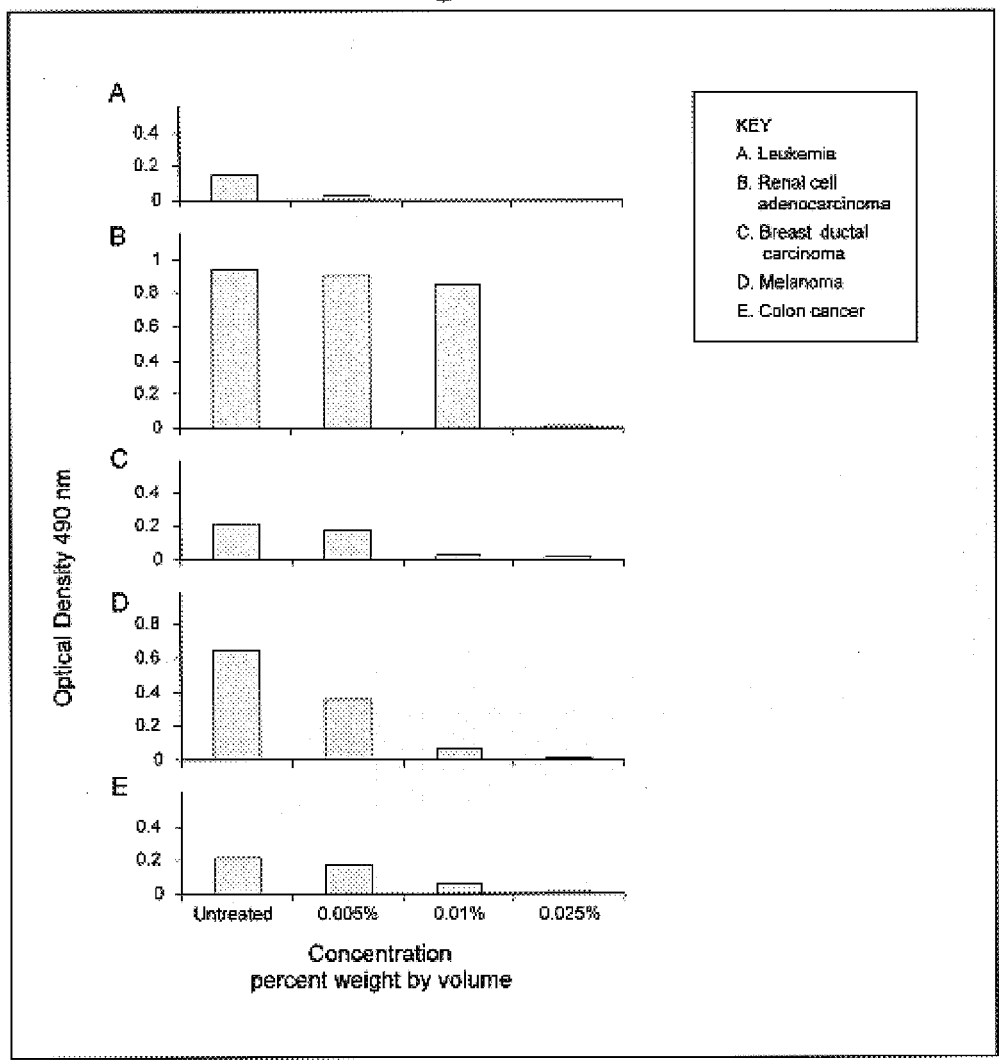
FIG. 5. Growth Assay. Five specific lines of cancer cells, representing the most invasive cancers, were seeded in equal numbers on a plate containing varying concentrations of oleuropein. After 5 days cell numbers were assessed using the MTS assay and optical density (490 nm) values are shown on the y-axis of the graph. The x-axis represents the concentration of oleuropein. No manipulation of the data was performed. These represent true and raw counts made on a microplate reader. In all cancers studied, oleuropein effectively inhibited growth.

Unregulated cell growth is the hallmark of cancer. This example illustrates the anti-cancer properties of oleuropein in the cell growth assay. Cancer cells, representing the most invasive cancers, were seeded in equal numbers on a plate containing varying concentrations of oleuropein. After 5 days cell numbers were assessed using the MTS assay and optical density (490 nm) values are shown on the y-axis of the graph (FIG. 5). The x-axis represents the concentration of oleuropein. These represent true and raw counts made on a microplate reader. In all cancers studied, oleuropein effectively inhibited growth.

Example 4

Figure 6:
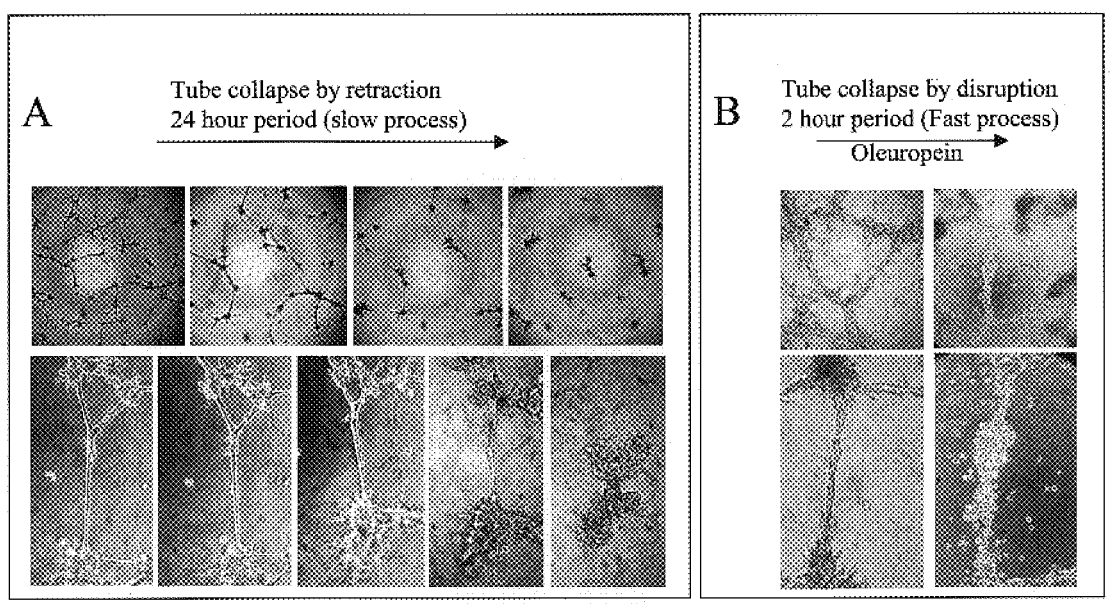
FIG. 6. Tube-disruption assay on Matrigel. Cells plated on matrigel form tube networks that collapse into clumps within 24-48 hours (FIG. 6A, top row). A close-up view of the tube collapse process demonstrates that it occurs by tube retraction where the nodes (where tubes intersect) are brought closer to one another and merge (FIG. 6A, bottom row). Individual cells remain elongated throughout. This slow process (24-48 hours) of cell motility and contraction involves active cytoskeletal reorganization. The addition of 0.1% oleuropein to the preformed tubes "rounds-up" or induces spherical shaping of individual cells in situ through a fast process occurring within 2 hours (FIG. 6B), disrupting the tubular network. Based on the understanding that spherically shaped or rounded cells don't move and remain in place indefinitely, thus the retraction process is aborted by the thwarting of cellular motility through the prevention of cytoskeletal reorganization.
Figure 7:
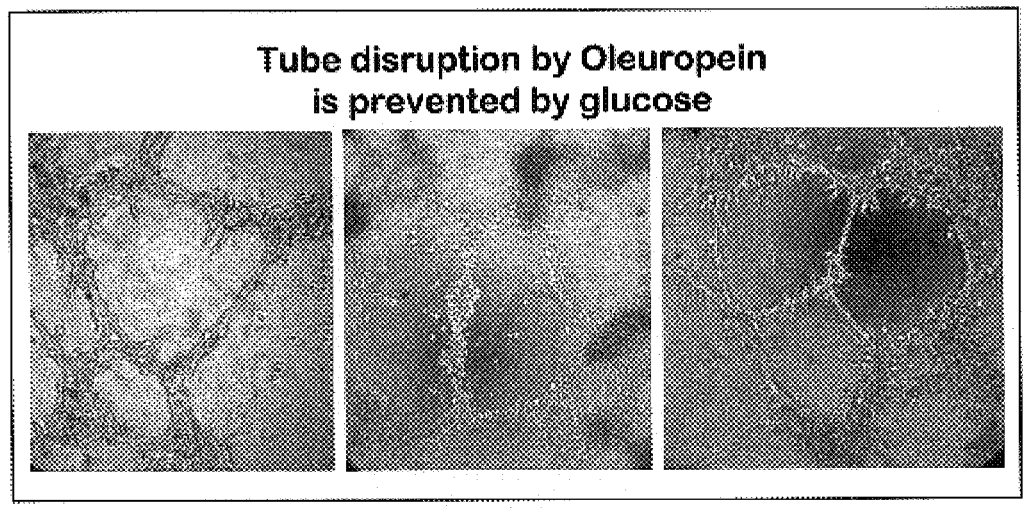
FIG. 7. Tube-disruption assay on Matrigel. Glucose-inhibited cellular rounding, which occurred by the addition of oleuropein.

This example illustrates oleuropein's effect on the cellular cytoskeleton by the tube-disruption assay. In this assay cells plated on matrigel form tube networks that collapse into clumps within 24-48 hours (FIG. 6A, top row). A close-up view of the tube collapse process demonstrates that it occurs by tube retraction where the nodes (where tubes intersect) are brought closer to one another and merge (FIG. 6A, bottom row). Individual cells remain elongated throughout. This slow process (24-48 hours) of cell motility and contraction involves active cytoskeletal reorganization. The addition of oleuropein to the preformed tubes rounds-up individual cells in situ through a fast process occurring within 2 hours (FIG. 6B), disrupting the tubular network. Rounded cells don't move and remain in place indefinitely. Thus the retraction process is aborted by the thwarting of cellular motility through the disruption of the cellular cytoskeleton and preventing its reorganization. This property by oleuropein was inhibited by glucose, indicating that oleuropein enters the cell through the glucose transporter and glucose competes with this transport (FIG. 7).

Example 5

This example illustrates the effect of oleuropein on wound healing in the in the cell migration assay. In this example oleuropein's effect on the cellular cytoskeleton and cell rounding is demonstrated. This example also illustrates the reversibility of oleuropein's effect on the cells suggesting minimal side-effects.

Figure 8:
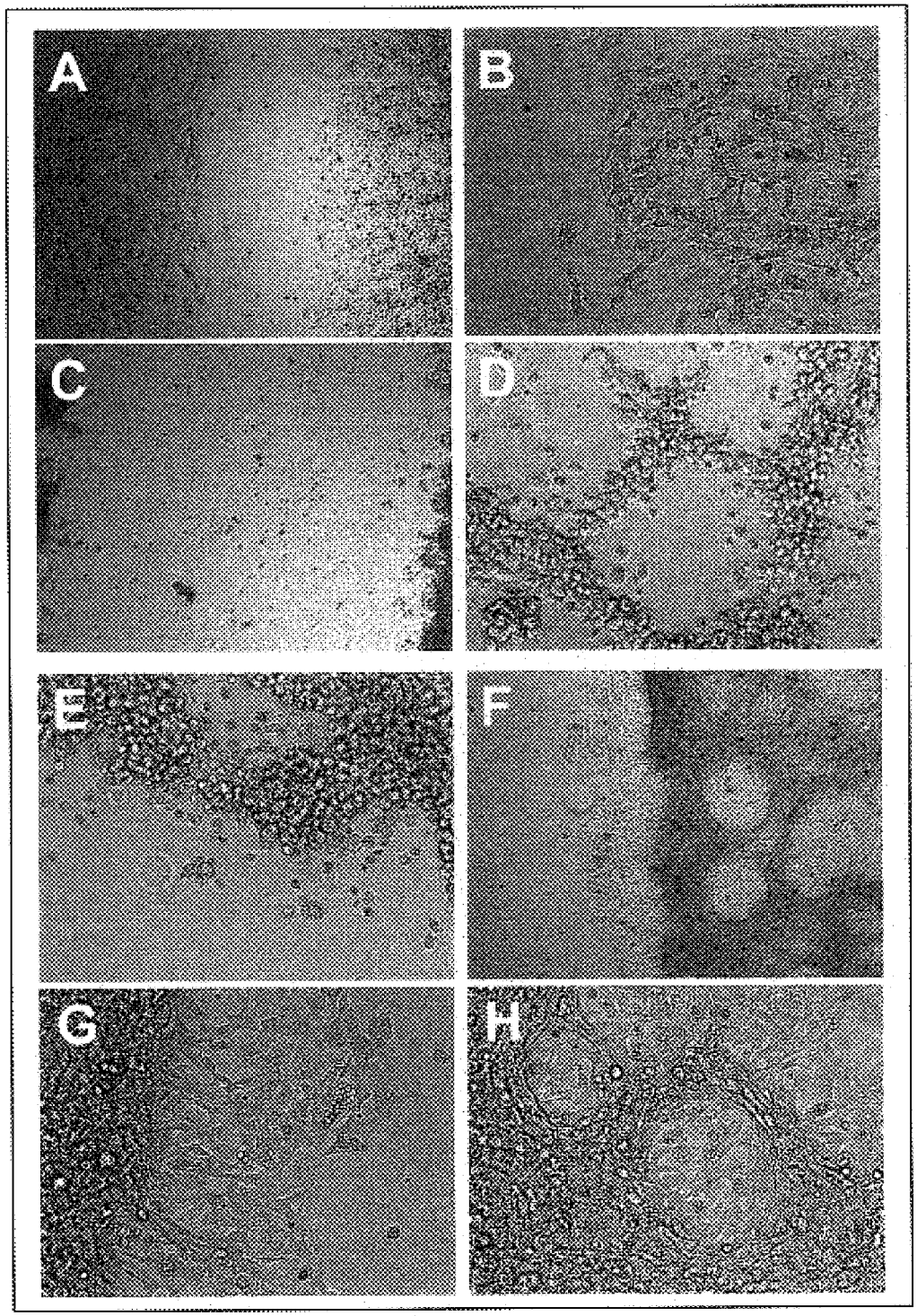
FIG. 8. Cell migration assay. Rabbit skin fibroblast cells were grown to a confluent monolayer of cells, which was subsequently wounded with a sterile wooden stick. The cells were then incubated and allowed to repair the wound in the culture. Untreated cells successfully migrated across the wounded area (A). Cells treated with oleuropein (0.01%) shown in (C) were effectively inhibited. A closer look at the oleuropein treated cells show a discontinuity in the cellular monolayer (D and E), due to the sphelical shaping or rounding-up of the cells as a result of oleuropein's effect on the cell's cytoskeleton. In contrast, untreated cells appear flat (B). Washing oleuropein from the cells reversed the rounding up process. The cells flatened, filled up the discontinuity in the monolayer (H) and began to migrate from the edge of the wound (F and G).

Rabbit skin fibroblast cells were grown to a confluent monolayer of cells, which was subsequently wounded with a sterile wooden stick. The cells were then incubated and allowed to repair the wound in the culture. Untreated cells successfully migrated across the wounded area FIG. 8A. Cells treated with oleuropein (0.01%) shown in FIG. 8C were effectively inhibited. A closer look at the oleuropein treated cells show a discontinuity in the cellular monolayer FIGS. 8D and 8E, due to the cells rounding up as a result of oleuropein's effect on the cell's cytoskeleton. In contrast, untreated cells appear flat FIG. 8B. Washing oleuropein from the cells reversed the rounding up process. The cells flattened, filled up the discontinuity in the monolayer (H) and began to migrate from the edge of the wound FIGS. 8F and 8G.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention. In this regard, it is contemplated that the methods of the present invention may further find therapeutic applications beyond those disclosed herein, as well as in addition to those disclosed and claimed in Applicants' Pending U.S. patent application Ser. No. 10/153,003.

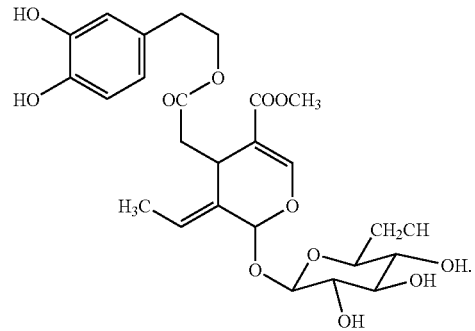

What is claimed is:

1. A method for treating cancer in a subject, wherein the cancer is selected from the group consisting of colon cancer, renal adenocarcinoma, and melanoma;

the method comprising administering to a subject in need of such treatment a therapeutically effective amount of a pharmaceutical composition having chemopreventive activity which contains as an active ingredient a therapeutically effective quantity of a compound of the formula or its enantiomer:

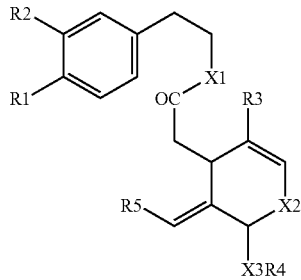

wherein R1 and R2 are functional groups selected from the group of hydroxyl, —NH2, —SH;

R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;

X1-X3 are functional groups selected from the group consisting of oxygen, sulfur, —CH2—, or carboxy;

R4 is a functional group selected from the group consisting of hydrogen, C1-C6-alkoxy, glucose, B-D-glucopyranose, C1-C6-alkyl, C2-C6-alkenyl, C2-C6-alkynyl, aryl, hydroxyl, halogen NO2, NH3, carbohydrate, amino acid, nucleotide and lipid; and R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3, and CH3.

2. A method of inhibiting the growth, motility, invasiveness and metastasis of cancer cells, wherein the cancer cells are selected from the group consisting of colon cancer, renal adenocarcinoma, and melanoma;

the method comprising contacting said cells with a pharmaceutical composition in an amount sufficient to inhibit the cancer or recurrence thereof, said pharmaceutical composition containing a therapeutically effective amount of a compound of the following formula or its enantiomer:

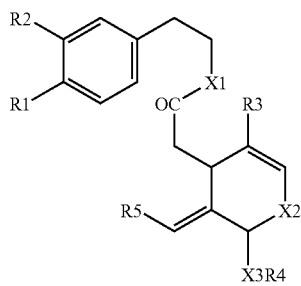

wherein R1 and R2 are functional groups selected from the group consisting of hydroxyl, —NH2, —SH;

R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;

X1-X3 are functional groups selected from the group consisting of oxygen, sulfur, —CH2—, or carboxy;

R4 is a functional group selected from the group consisting of hydrogen, C1-C6-alkoxy glucose, B-D-glucopyranose, C1-C6-alkyl, C2-C6-alkenyl, C2-C6-alkynyl, aryl, hydroxyl, halogen NO2, NH3, carbohydrate, amino acid, nucleotide, and lipid; and R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and CH3.

3. The method of claim 2 wherein said inhibition of the survival, growth, motility, invasiveness and metastasis of cancer cells occurs in vivo.

4. The method of claim 2 wherein said inhibition of the survival, growth, motility, invasiveness and metastasis of cancer cells occurs in vitro.

5. A method for treating cancer in a subject, wherein said cancer is selected from the group consisting of colon cancer, renal adenocarcinoma, and melanoma;

said method comprising administering to a subject in need of such treatment a therapeutic amount of a pharmaceutical composition operative to effectuate anti-survival, anti-growth, anti-motility, anti-invasiveness and anti-metastasis activity associated with said cancer, the pharmaceutical composition containing as an active ingredient at least one composition produced by the hydrolysis of a compound of the following formula or its enantiomer:

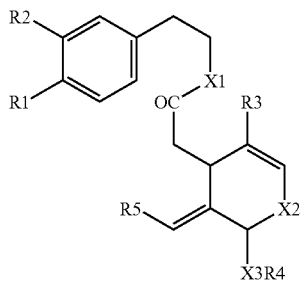

wherein R1 and R2 are functional groups selected from the group consisting of hydroxyl, —NH2, —SH;

R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;

X1-X3 are functional groups selected from the group consisting of oxygen, sulfur, —CH2—, or carboxy;

R4 is a functional group selected from the group consisting of hydrogen, C1-C6-alkoxy, glucose, B-D-glucopyranose, C1-C6-alkyl, C2-C6-alkenyl, C2-C6-alkynyl, aryl, hydroxyl, halogen NO2, NH3, carbohydrate, amino acid, nucleotide and lipid; and R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3, and CH3.

6. A method of inhibiting cancer cell growth comprising contacting the cancer cells with a pharmaceutical composition in an amount sufficient to inhibit growth thereof, wherein said cancer cells are selected from the group consisting of colon cancer, renal adenocarcinoma, and melanoma;

said pharmaceutical composition containing a therapeutically effective amount of a compound selected from the group consisting of at least one composition produced by the hydrolysis of a compound of the following formula or its enantiomer:

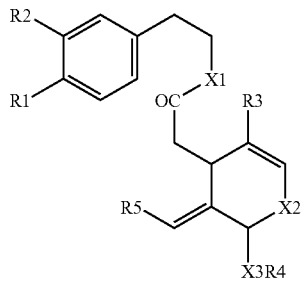

wherein R1 and R2 are functional groups selected from the group consisting of hydroxyl, —NH2, —SH;
R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;
X1-X3 are functional groups selected from the group consisting of oxygen, sulfur, —CH2—, or carboxy;
R4 is a functional group selected from the group consisting of hydrogen, C1-C6-alkoxy, glucose, B-D-glucopyranose, C1-C6-alkyl, C2-C6-alkenyl, C2-C6-alkynyl, aryl, hydroxyl, halogen NO2, NH3, carbohydrate, amino acid, nucleotide and lipid; and
R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3, and CH3.

7. The method of claim 1 wherein said composition comprises the following formula or its enantiomer:

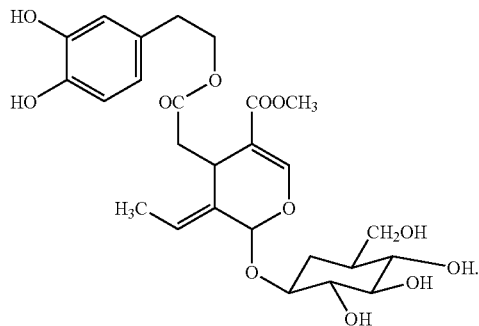

8. The method of claim 2 wherein said composition comprises the following formula or its enantiomer:

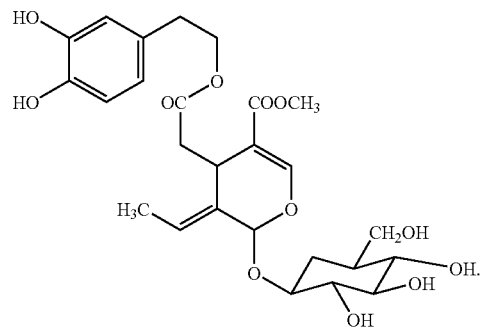

9. A method of treating cancer in an animal in need of such treatment, wherein said cancer is selected from the group consisting of colon cancer, renal adenocarcinoma, and melanoma;
said method comprised of administering to said patient a therapeutically effective amount of a compound having the following structure or it enantiomer:

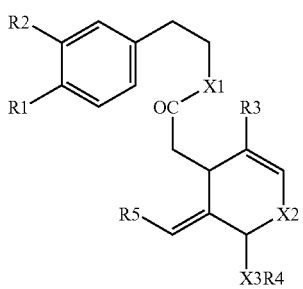

wherein R1 and R2 are functional groups selected from the groups consisting of hydroxyl, —NH2, —SH;
R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;
X1-X3 are functional groups selected from the group consisting of oxygen, sulfur, —CH2—, or carboxy;
R4 is a functional group selected from the group consisting of hydrogen, C1-C6-alkoxy, glucose, B-D-glucopyranose, C1-C6-alkyl, C2-C6-alkenyl, C2-C6-alkynyl, aryl, hydroxyl, halogen NO2, NH3, carbohydrate, amino acid, nucleotide, and lipid; and
R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3, and CH3;

or a pharmaceutically acceptable salt, prodrug or hydrate thereof.

10. The method of claim 1 wherein said composition is formulated as a tablet or elixir for oral administration.

11. The method of claim 1 wherein said composition is administered via a route selected from the group consisting of intramuscular or intravenous administration.

12. The method of claim 1 wherein said composition is administered via inhalation.

13. The method of claim 9 wherein said compound is administered via a route selected from the group consisting of oral, buccal, rectal, parenteral, intraperitoneal, intradermal, transdermal, and intracheal.

14. The method of claim 9 wherein said composition is formulated as a tablet or elixir for oral administration.

15. The method of claim 9 wherein said composition is administered via a route selected from the group consisting of intramuscular or intravenous administration.

16. The method of claim 9 wherein said composition is administered via inhalation.

17. The method of treating cancer in accordance with claim 9 wherein said composition comprises the following formula or its enantiomer:

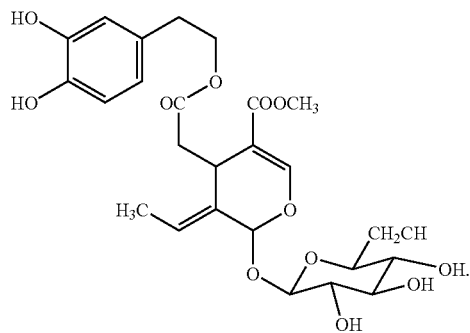

18. The method of claim 5 when said at least one composition is selected from the group consisting of oleuropein aglycone, elenolic acid, beta-3, 4,-dihydroxyphenyethyl alcohol and methyl-o-methyl elenolate.

19. A method of treating cancer in a subject in need thereof, the cancer being selected from the group consisting of leukemia, renal cell adenocarcinoma, breast ductal carcinoma, melanoma and colon cancer, the method comprising administering to said subject a therapeutically effective amount of a pharmaceutical composition, said pharmaceutical composition containing a therapeutically effective amount of a compound of the following formula or its enantiomer:

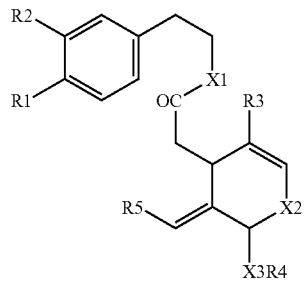

wherein R1 and R2 are functional groups selected from the group consisting of hydroxyl, —NH2, —SH;

R3 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and COOCH3;

X1-X3 are functional groups selected from the group consisting of oxygen, sulfur, —CH2—, or carboxy;

R4 is a functional group selected from the group consisting of hydrogen, C1-C6-alkoxy, glucose, B-D-glucopyranose, C1-C6-alkyl, C2-C6-alkenyl, C2-C6-alkynyl, aryl, hydroxyl, halogen NO2, NH3, carbohydrate, amino acid, nucleotide, and lipid; and R5 is a functional group selected from the group consisting of hydrogen, C1-C6-alkyl, C2-C6-alkenyl, C2-C6-alkynyl, aryl, hydroxyl, C1-C6-alkoxy, halogen, NO2, NH3 and CH3.

20. The method of claim 19 wherein the R4 moiety is B-D-glucopyranose and said composition comprises the following formula or its enantiomer: